United States Patent [19]

Freeman et al.

[11] Patent Number: 4,659,665
[45] Date of Patent: Apr. 21, 1987

[54] ENZYME MEMBRANES FOR ELECTRODES

[75] Inventors: Amihay Freeman, Ben-Shemen; Ruth Tor, Kiryat Ono, both of Israel

[73] Assignee: Ramot University Authority for Applied Research and Industrial Development Ltd., Tel-Aviv, Israel

[21] Appl. No.: 642,245

[22] Filed: Aug. 20, 1984

[30] Foreign Application Priority Data

Sep. 2, 1983 [IL] Israel ............................................ 69644

[51] Int. Cl.$^4$ .................... C12N 11/04; C12N 11/14; C12N 11/08; C12M 1/40
[52] U.S. Cl. .................................. 435/182; 204/403; 435/176; 435/180; 435/288; 435/817
[58] Field of Search ............... 435/174, 176, 180, 182, 435/288, 817; 204/403

[56] References Cited

U.S. PATENT DOCUMENTS 3,542,662  11/1970  Hicks et al. ..................... 435/288 X

OTHER PUBLICATIONS

Freeman, Gel Entrapment of Whole Cells and Enzymes in Crosslinked, Prepolymerized Polyacrylamide Hydrazide, Enzyme Engineering, 7, vol. 434.
Freeman et al., New Enzyme Membrane for Enzyme Electrodes, Analytical Chemistry, 1986.
Durand et al., An Enzyme Electrode for Acetylcholine, Biochimica et Biophysica Acta, 527, (1978), 277–281.
Freeman et al., Immobilization of Microbial Cells in Crosslinked, Prepolymerized, Linear Polyacrylamide Gels: Antibiotic Production by Immobilized Streptomyces Clavuligerus Cells, Biotechnology and Bioengineering, vol. XXIII, pp. 2747–2759 (1981).
Nilsson et al., Determination of Glucose, Urea and Penicillin Using Enzyme-pH-Electrodes, Biochimica et Biophysica Acta, 320, (1973), 529–534.
Guilbault et al, Improved Urea Electrode, Analytical Chemistry, vol. 45, No. 2, Feb. 1973.
Bowers et al, Immobilized Enzymes in Analytical Chemistry, Advanced Biochem. Eng. 15, 89–129, 1980.

*Primary Examiner*—David M. Naff
*Attorney, Agent, or Firm*—Fleit, Jacobson, Cohn & Price

[57] ABSTRACT

A film or membrane containing a biologically active protein such as an enzyme is prepared from a polymer substituted with acyl hydrazide groups. Preferably, the polymer is an acrylamide/methacrylamide copolymer in the ratio of about 70/30, and the film or membrane is about 30–100 microns thick. The film or membrane is prepared on an electrode and crosslinked to produce an enzyme electrode.

8 Claims, 1 Drawing Figure

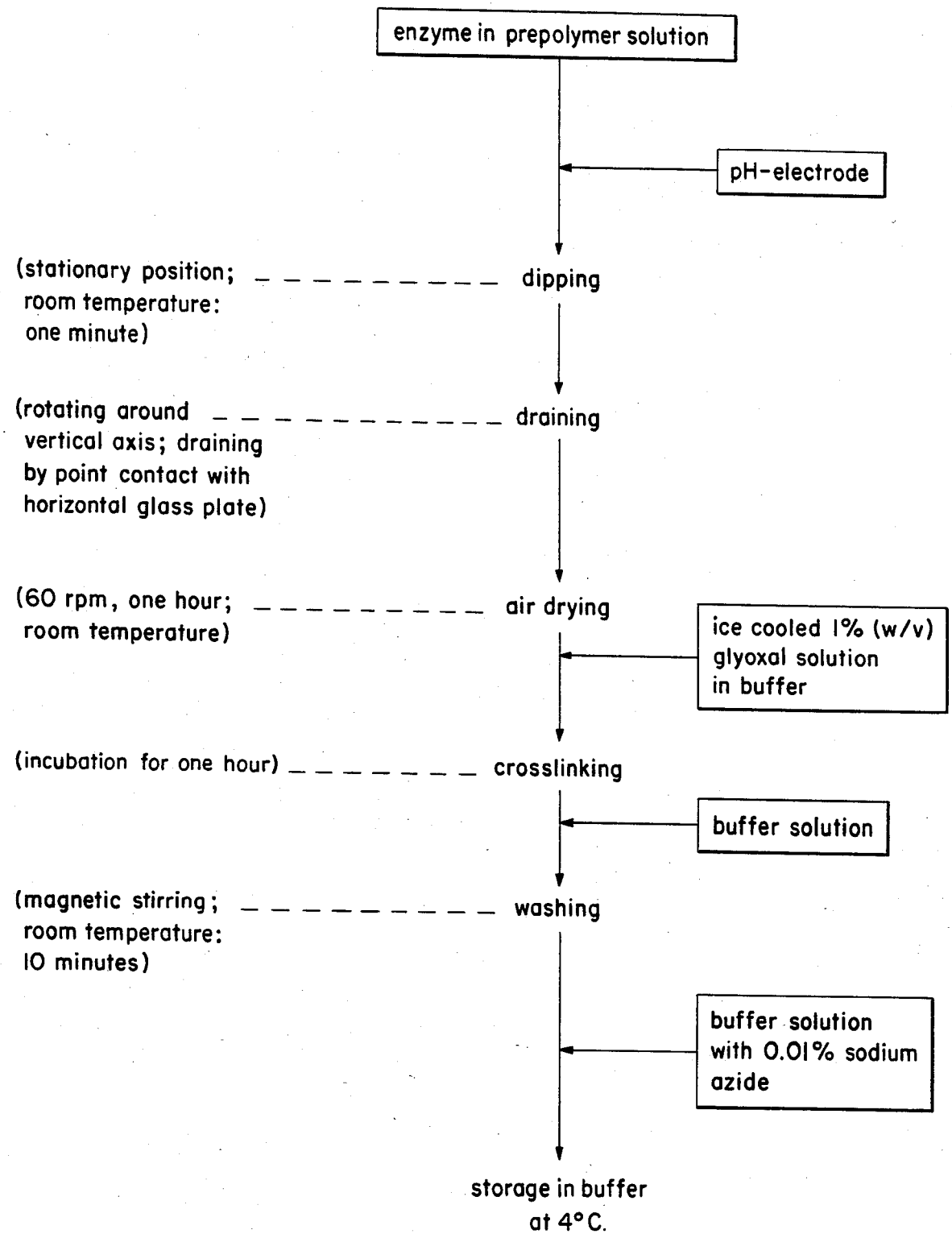

ENZYME MEMBRANES FOR ELECTRODES

FIELD OF THE INVENTION

There are provided novel membranes containing proteins characterized by their biological activity, and especially membranes containing active enzymes. There are also provided membranes containing biologically active proteins adhering to solid substrates, and particularly enzyme membranes containing enzymes adhering to the surface of an electrochemical sensor, constituting an enzyme electrode. There is also provided a process for the production of such membranes and for producing such membranes adhering to desired solid substrates.

BACKGROUND OF THE INVENTION

The use of various membranes containing biologically active proteins, and especially membranes containing enzymes has become widespread in recent years. Also other means for the immobilization of enzymes have been resorted to.

In such enzyme electrodes the electrochemical sensors detect changes in the concentration of a product, a cosubstrate or a cofactor involved in the enzymatic conversion. The signal obtained is thus proportional to the concentration of the substrate. Enzyme electrodes are highly specific and allow for easy processing and control of repeated or continuous analysis (see Bowers, L. D. and Carr, P. W. Adv. Biochem. Eng. 15, 89-199, 1980).

In recent years several methods were developed for the construction of enzyme electrodes. These include physical entrapment of soluble enzyme by means of dialysis membrane (see Nilsson, H. et al. Biochem. Biophys. Acta 320, 529-534 (1973); physical gel entrapment of the enzyme in a gel layer, formed by radical polymerization of water soluble vinyl monomers in presence of the enzyme and fine nylon net (as a mechanical support) (see Nilsson, H. et al, ibid and Guilbault, G. G. and Nagy, G. Anal. Chem. 45, 417-419 (1973)); and cross-linking of the enzyme with inert protein by means of glutardialdehyde (see Durand, P. et al, BBA, 527, 277-281 (1978)).

The immobilization technique employed for the preparation of the enzyme membrane strongly affects the operational parameters of the enzyme electrode—the range of substrate concentrations that may be detected, response time, wash time and storage and operational stability.

The combination of enzyme membranes with electrochemical sensors, such as pH electrodes provides an efficient tool for use in analysis, research and fermentation industry.

One of the drawbacks of existing enzyme electrodes is the rather primitive attachment of the membrane in the pH electrode. Generally an attachment based on mechanical means, such as O-rings has been resorted to, generally with a protective material covering the membrane.

The present invention provides improved enzyme membranes and efficient means for the production of same. The method of production is fast, inexpensive and does not require complicated equipment. The novel enzyme electrodes have increased operational and storage capabilities compared with existing ones, increasing the efficiency and reproducibility of such devices.

The invention is illustrated in the following with reference to the production of enzyme electrodes. It ought to be clearly understood that the process of the invention can be used with a variety of other biologically active proteins, and that the resulting films or membranes can be bonded efficiently to various solid substrates due to their strong adhesivity to solids. They can be bonded to glass, porcelain, carbon and metals and thus various sensors and similar devices can be constructed.

SUMMARY OF THE INVENTION

The invention relates to novel polymers containing biologically active proteins, such polymers being characterized by a strong adherence to solid substrates; to a process for the production of same and to devices containing same. The invention further relates to enzyme membranes attached to solid surfaces, and especially to pH electrodes, constituting enzyme electrodes having a high degree of efficiency and reproducibility.

The invention further relates to membranes containing other biologically active proteins and to devices based on such membranes.

BRIEF DESCRIPTION OF THE DRAWING

The FIGURE is a flow diagram of the process according to the present invention.

DETAILED DESCRIPTION OF THE PREFERRED EMBODIMENT

The invention is based on the incorporation of biologically active proteins in a suitable polymer or copolymer, applying the solution to a substrate, crosslinking the polymer by a suitable cross-linking agent, such as glyoxal, resulting in a thin membrane of the desired properties which adheres to the solid substrate. According to a preferred embodiment of the invention an acrylamide-methacryl amide copolymer is used as backbone polymer, a solution of same is admixed with the biologically active protein, the film is formed on the desired substrate and crosslinked in situ. When this method is used for the production of enzyme electrodes, the membrane film is formed on a suitable pH electrode and cross-linked, resulting in a thin film which firmly adheres to the surface of the electrode.

A wide variety of enzymes can be used, representative examples being cholinestrase, urease and penicillinase. The response time and the substrate concentration range which can be detected depend to a large extent on the chemical nature, the concentration and the pH of the buffer employed. Various buffers which were found to give optimum results are set out in the following examples. The enzyme electrodes produced according to the present invention are characterized by the direct attachment of the enzyme membrane film to the pH electrode surface, without any mechanical supports or attachment means being required.

The novel enzyme electrodes are characterized by high operational and storage stability over prolonged periods of time. They have a wide linear range of response and a comparatively short response time. The novel membrane films can be applied to various substrates, and a good adherence is obtained with varying substrates such as glass, ceramics, carbon and metals.

Various copolymers can be used. The best results were obtained with cpolymers of acrylamide and methacrylamide substituted with acyl hydrazide groups. The copolymer is subsequently cross-linked by a cross-linking agent such as glyoxal.

Representative membrane films have a thickness of from about 30 to 100 microns, a preferred value being about 50 microns thickness of the film. The resulting enzyme gel layer adheres well to the pH electrode and forms the desired enzyme electrode.

There may be used acrylamide by itself, but better results are obtained by using copolymers of acrylamide and methacrylamide in a ratio of about 70:30 by molar ratio, which is partially substituted with acylhydrazide functional groups. Typical values of acyl hydrazide content were of the order of 750 to 850 micromol per gram of dry polymer.

The polymer or copolymer solution is applied to the solid substrate by any conventional technique, the most simple being by dipping if same is to be applied to the surface of a pH electrode. When a surface film is desired in a flat solid substrate, brushing, dipping or any other technique may be resorted to.

EXAMPLE 1

(a) Preparation of polymeric moiety

Linear, water soluble acrylamide-methacrylamide copolymer (monomer ratio 70:30), partially substituted with acylhydrazide functional group was prepared by a modification to the method previously described for the acrylamide homopolymer analogue (see Freeman, A. and Aharonowitz, Y. Biotech. Bioeng. 23, 2747-2759 (1981)). In a 1 liter round-bottomed flask equipped with a magnetic stirrer, were added 21 g (0.3 mole) acrylamide and 10.8 g (0.13 mole) methacrylamide, in 150 ml water. The solution was brought to 40° C. and 50 ml of 0.092M TEMED N,N',N':tetramethyl-ethylenediamine followed by 150 ml of 0.0175M ammoniumpersulphate. Polymerization was allowed to proceed in the closed vessel for 1 h at 40° C. Water (400 ml) was then added and the temperature adjusted to 50° C. Hydrazine hydrate (225 ml, final concentration 4.75M) was then added and hydrazinolysis was carried out for 3 h at 50° C. The polymer solution was then cooled and the polymer separated by precipitation in ice-cooled methanol (5 l). The polymer was separated by filtration, dissolved in 350 ml water and reprecipitated. Following filtration the polymer was incubated in methanol (2 hrs at room temperature) separated, dried on a rotary evaporator and finally stored, dessicated, in vacuum over $P_2O_5$ overnight. The polymer can be stored at $-18°$ C. for periods exceeding several days.

(b) Preparation of copolymer and enzyme solution

Acrylamide-methacrylamide copolymer was dissolved in distilled water with slow magnetic stirring at room temperature to make a 25% (w/v) solution. Into this solution 2M phosphate, pH 7.5, was added to make a final concentration of 0.014, followed by the addition of enzyme stock solution (6600 units/ml electric eel acetylcholine-esterase, in 0.1M phosphate, pH 8, containing 0.01% (w/v) gelatin) to give a final enzyme concentration of 500 enzyme units/ml at a final polymer concentration of 20% (w/v).

(c) Preparation of enzyme membrane -pH electrode conjugate

The membrane was prepared according to the process as set out in the FIGURE. A pH electrode was dipped into the enzyme and prepolymer solution in a stationary position at room temperature for one minute. The electrode was rotated around its vertical axis and drained by point contact with a horizontal glass plate. The electrode was then dried at room temperature for approximately one hour at a dryer speed of approximately 60 revolutions per minute. The membrane on the electrode was then crosslinked by an ice cooled 1% (w/v) glyoxal solution in buffer and was incubated for one hour. The electrode was washed in a buffer solution and stirred with a magnetic stirrer at room temperature for approximately 10 minutes. Finally, the electrode was stored in a buffer solution containing 0.01% sodium azide at 4° C.

(d) Determination of acetylcholine by means of acetylcholine esterase electrode

Acetylcholine esterase electrode was assayed at 25° C. in 5 mM HEPES buffer, pH 8, containing 20 mM $MgCl_2$, 0.1M NaCl and 0.01% (w/v) gelatin. Linear response (measured as $\Delta$mv recorded as result of adding said amounts of substrate into the reaction vessel) in the concentration range $2.10^{-5}$-$1.10^{-3}$M, with slope of 29.5 mv/M, and response time (time required to reach steady state measurement) of 0.5–4 minutes. This electrode, when stored at 4° C. and tested at 25° C., was stable for at least 6 months (over 180 measurements) with no significant decrease in linearity and slope of taken calibration curves.

EXAMPLE 2

By substituting Urease for Acetylcholine esterase (stock solution of 130 mg/ml in 0.01M phosphate, pH 7, containing 5 mM EDTA and 5 mM DTE, added to copolymer solution of 25% (w/v) to make a final solution of 3 mg/ml enzyme in 20% (w/v) copolymer with 0.1M phosphate, pH 7 and 5 mM EDTA, and 5 mM DTE), an urease-ph electrode was obtained. Urea determination, at 30° C., in 10 mM Histidine buffer, pH 7.6, with 5 mM EDTA and 5 mM DTE, was possible with linear response in the range of $2.10^{-5}$-$3.10^{-4}$M with a slope of 109 mv/M, with response time of 2.8–6.4 minutes. The electrode was stable for at least two months. Though during this period of time decrease in the slope of the calibration curve of about 50% was observed, a linear response was maintained.

EXAMPLE 3

By substituting $\beta$-lactamase for acetylcholine esterase (stock solution of 2500 units/ml in 0.01M phosphate, pH=7, added to copolymer solution of 25% (w/v) to make final solution of 500 units/ml enzyme in 20% (w/v) copolymer solution with 0.1M phosphate pH 7penicillinase -pH electrode was obtained.

Penicillin G determination, at 25° C., in 0.01M phosphate, pH 8, was possible with linear response in the range of $4.10^{-5}$-$1.2.10^{-3}$M, with a slope of 14 mv/M, with response time of 2.4–4.2 minutes. This electrode showed no decrease in activity when stored at 4° C. and assayed at 25° C. for at least the 5 weeks tested.

We claim:

1. A membrane or film comprising an acrylamide/methacrylamide copolymer in a respective molar ratio of about 70/30, substituted with acyl hydrazide groups, crosslinked with a crosslinking agent and containing a biologically active protein, said membrane or film having a thickness of about 30 to 100 microns.

2. A membrane of film according to claim 1, wherein the protein is an enzyme.

3. A membrane or film according to claim 1, wherein the cross-linking agent is glyoxal.

4. An enzyme electrode comprising a pH electrode coated with a membrane film according to claim 1 wherein the biologically active protein is an enzyme, and where the film containing the enzyme adheres to the effective surface of the electrode.

5. an enzyme electrode according to claim 4, wherein the crosslinking agent is glyoxal.

6. A process for the production of membranes or films containing a biologically active protein, adhering to solid substrates, which comprises preparing an aqueous solution of an acrylamide/methacrylamide copolymer in a respective molar ratio of about 70/30 substituted with acyl hydrazide groups and the biologically active protein, applying a film of the solution to the solid substrate to obtain a film of the copolymer having a thickness of about 30 to 100 microns, and cross-linking the copolymer by contacting said copolymer with a solution of a cross-linking agent.

7. A process according to claim 6, wherein the cross-linking agent is glyoxal.

8. A process according to claim 6 wherein the solid substrate is a pH electrode.

* * * * *